United States Patent [19]

Itanami et al.

[11] 4,041,640
[45] Aug. 16, 1977

[54] CHLORELLA-CULTURING APPARATUS

[75] Inventors: Kojiro Itanami; Masanori Ishizaki, both of Fukuoka, Japan

[73] Assignee: Chlorella Industry Co., Ltd., Tokyo, Japan

[21] Appl. No.: 683,530

[22] Filed: May 5, 1976

[30] Foreign Application Priority Data

Dec. 22, 1975 Japan .................. 50-151968
Mar. 1, 1976 Japan .................. 51-22021

[51] Int. Cl.² ........................................ A01G 33/00
[52] U.S. Cl. .............................. 47/1.4; 259/114
[58] Field of Search .............. 47/1.4; 259/99, 104, 259/108–109, 114

[56] References Cited

U.S. PATENT DOCUMENTS

| 3,295,835 | 1/1967 | Klopper | 259/108 |
| 3,414,239 | 12/1968 | Eirich et al. | 259/104 |
| 3,476,364 | 11/1969 | Thomson | 259/108 |
| 3,986,297 | 10/1976 | Ichimora et al. | 47/1.4 |

Primary Examiner—Robert E. Bagwill
Attorney, Agent, or Firm—Carroll F. Palmer

[57] ABSTRACT

A chlorella-culturing apparatus comprises a rotatable arm body fitted with a stirring mechanism for forcefully producing stirring streams by stirring blades and scraping mechanism. The scraping mechanism is so mounted on the rotatable arm body as to slide up and down. It is brought down when the chlorella-culturing apparatus discharges cultured chlorella, and rotated with the arm body in contact with a bottom board and inner peripheral surface of a chlorella-culturing tank. At least one chlorella-discharging groove is formed in the bottom board of the chlorella-culturing tank. Deposits removed by the scraping mechanism are carried together with a chlorella-culturing liquid into the discharging groove by the scraping mechanism. The central pillar and side wall of the chlorella-culturing tank have an inclined surface which is sprayed with water to prevent cultured chlorella and any other material from being deposited on said surface.

9 Claims, 9 Drawing Figures

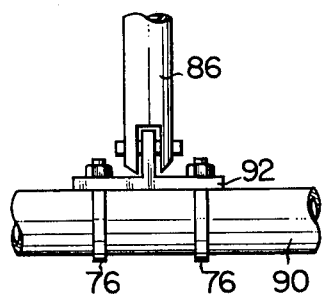
FIG. 4
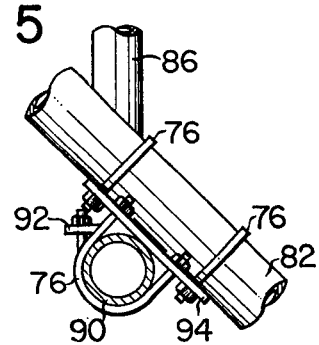
FIG. 5
FIG. 6
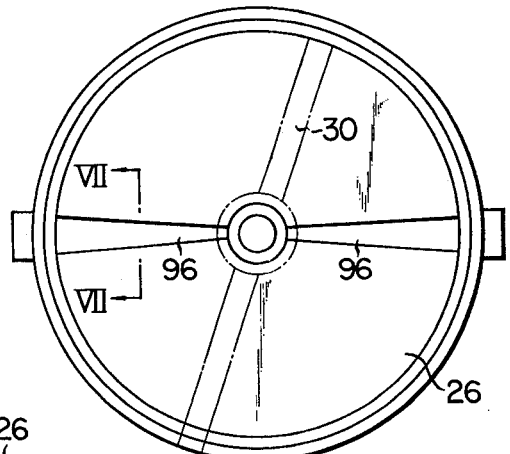
FIG. 7
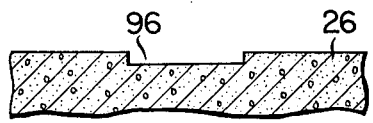
FIG. 8
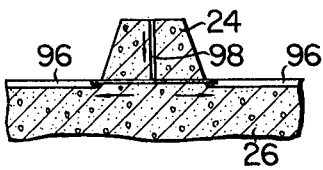
FIG. 9
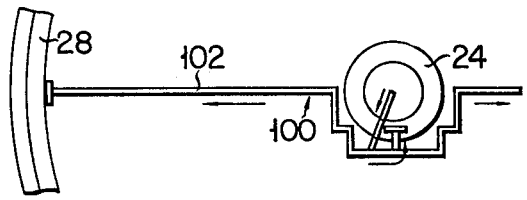

CHLORELLA-CULTURING APPARATUS

BACKGROUND OF THE INVENTION

This invention relates to a chlorella-culturing apparatus capable of efficiently culturing chlorella. The customary industrial process of culturing chlorella was to charge chlorella and culturing liquid in a shallow circular water tank, stir the mixed mass while introducing carbon dioxide gas thereinto, and apply a required amount of light on the chlorella floating on the chlorella-culturing liquid. With the conventional industrial chlorella-culturing device, a stirring mechanism was fixed to the lower part of a rotatable arm body to rotate therewith for stirring. Though stirring streams were forcefully generated by the stirring blades in the chlorella-culturing tank, bacilli contained in the chlorella-culturing liquid and chlorella itself tended to precipitate and disposite on the bottom board and inner side walls of the chlorella-culturing tank, because the tank charge was left intact for a long time. Obviously, such deposition contaminated cultrued chlorella and restricted its growth in the pure form. Before, therefore, the chlorella-culturing tank was again charged with a fresh batch of chlorella mixed with a culturing liquid, it was necessary to remove deposits produced in the preceding culturing step from the culturing tank. However, the known chlorella-culturing apparatus was not provided with means for automatically scarping off such deposits to clean the interior of the chlorella-culturing tank. Consequently an operator manually took off deposits from the culturing tank by means of, for example, a brush. As naturally expected, the culturing tank had to be emptied, before the deposits could be manually removed. Accordingly, the customary chlorella-culturing apparatus failed to culture chlorella continuously, presenting difficulties in the efficient growth of chlorella.

Further with the prior art chlorella-culturing apparatus, the bottom board of the chlorella-culturing tank was inclined to cause the liquid therein gravitationally to flow to the tank outlet. Moreover, cultured chlorella was discharged together with a culturing liquid by a stirring mechanism mounted at prescribed position on the rotatable arm body. This arrangement consumed a great deal of time in removing the cultured chlorella, presenting difficulties in carrying out in quick and efficient exchange of a treated mixture of chlorella and culturing liquid for a fresh one.

This invention has been accomplished in view of the above-mentioned circumstances and is intended to provide an improved chlorella-culturing tank whose interior is kept clean for the efficient growth of chlorella.

SUMMARY OF THE INVENTION

According to a preferred embodiment of this invention, there is provided a chlorella-culturing apparatus, wherein a scarping mechanism is so mounted on a rotatable arm body as to slide up and down. The scraping mechanism is brought down where a mass charged in a chlorella-culturing tank is drawn out and rotated with the arm body in contact with the inner peripheral wall and bottom board of the chlorella-culturing tank, thereby removing deposits precipitated and gathered on said inner peripheral wall and bottom board. A plurality of, for example, two discharging grooves radially extend in symmetrical relationship with respect to the center of the central pillar are formed in said bottom board.

When the scraping mechanism is rotated, a treated mixture of cultured chlorella and culturing liquid, as well as deposits settled on the inner peripheral wall and bottom board of the chlorella-culturing tank, are quickly drawn out through the discharging grooves.

Cultured chlorella tends to be deposited not only on the inner wall of the chlorella-culturing tank but also on the surface of the stirring mechanism, particularly that of the stirring blades, because the stirring mechanism is immersed in the culturing liquid during the chlorella-culturing step. Deposition of cultured chlorella undesirably obstructs its growth and decreases the stirring efficiency. Therefore, the stirring blades must always be kept clean. With the prior art chlorella-culturing apparatus, however, the stirring mechanism was fixed to the underside of the rotatable arm body, and the stirring blades were not so positioned as to face the rotatable arm body in order to elevate the stirring efficiency, presenting difficulties in washing the stirring blades from the rotatable arm body during the chlorella-culturing step. Consequently, after the chlorella-culturing tank was emptied, an operator entered the tank and washed the stirring blades by spraying water thereon.

It is therefore preferred that the stirring mechanism, particularly stirring blades be so mounted on the rotatable arm body as to swing independently of the rotating of the arm body in order to mechanically wash the stirring blades without requiring an operator to enter the chloella-culturing tank.

BRIEF DESCRIPTION OF THE DRAWINGS

This invention can be more fully understood from the following detailed description when taken in conjunction with the accompanying drawings, in which:

FIGS. 4 and 5 respectively are a front view and side elevation showing the manner in which a piston-cylinder assembly is coupled to a lower connecting rod;

FIG. 6 is a schematic plan view of the bottom board of the chlorella-culturing apparatus of FIG. 1 in which two discharging grooves are formed;

FIG. 7 is a cross sectional view of the discharging groove on line VII—VII of FIG. 6;

FIG. 8 is a cross sectional view of high voltage current-generating means embedded in the central pillar of a chlorella-culturing tank; and FIG. 9 is a front view of means for spraying water on the inner peripheral wall of the chlorella-culturing tank.

Referring to FIGS. 1 and 2, a chlorella-culturing apparatus 20 according to this invention is provided with a chlorella-culturing tank 22 whose central pillar 24 takes a normally positioned frusto-conical form, whose bottom board 26 is inclined downward in a radial direction toward the outside and whose side wall 28 has a cross section so shaped as to cause the lower portion to be drawn nearer to the central pillar 24. A rotatable arm body 30 is stretched across the central pillar 24 and side wall 28 of the chlorella-culturing tank 22. This arm body 30 is made to rotate about the central pillar 24 by the known power source (not shown). The arm body 30 is made mechanically strong by being constructed of, for example, plate steel or angle steel, and concurrently constitutes an operator's footpatch extending from the side wall 28 to the central pillar 24. Referential numerals 34, 35 respectively denote the handrail of the operator's footpath 32 and that of a control tower 36 positioned above the central pillar 24.

Figure 1:
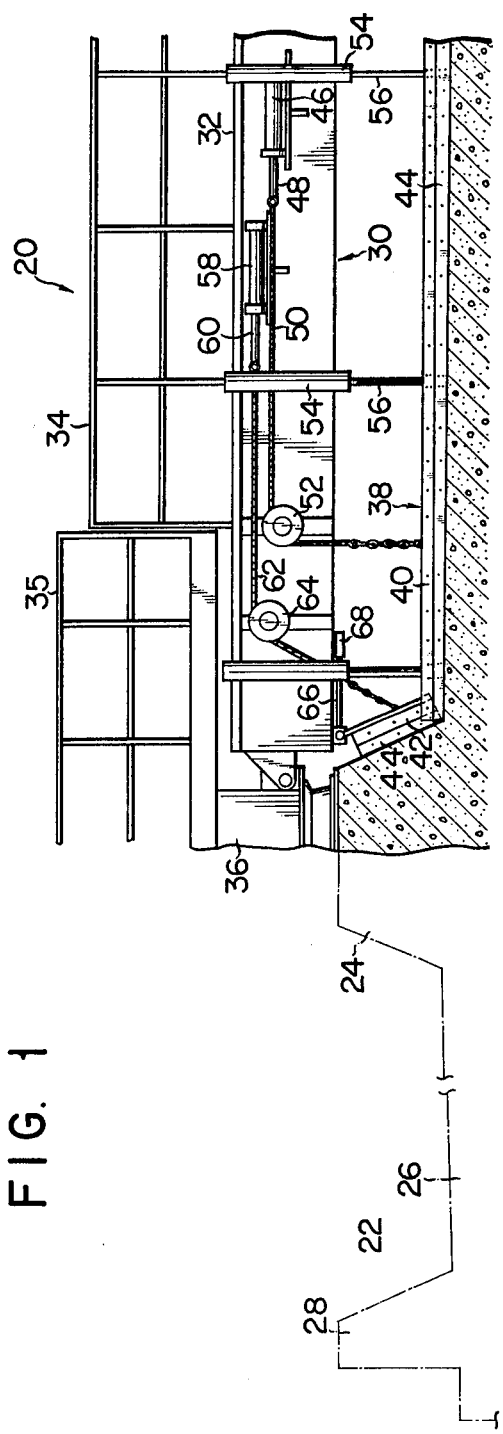
FIG. 1 is a fragmentary schematic cross sectional view of an improved chlorella-culturing apparatus embodying this invention.

A scraping mechanism 38 is fitted to the rear corner side of the rotatable arm body 30 so as to slide vertically. This scraping mechanism 38 comprises a central scraper 40 touchable to the bottom board 26 of the chlorella-culturing tank 22 and two end scrapers 42 touchable to the inclined side wall 28 of the chlorella-culturing tank 22 and the inclined wall of the frusto-conical central pillar 24 respectively. A flexible scraping member 44 made of, for example, hard rubber is bolted to the lower end of the central scraper 40. Therefore, deposits on the bottom board 26 can be effectively removed without being affected by irregularities on the upper surface of the bottom board 26. A wire 50 with a chain is connected at one end to a piston rod 48 of a piston-cylinder assembly 46 of, for example, the pneumatic type, and at the other end to the central scraper 40 through an idler pulley 52 for vertical movement of the central scraper 40. A plurality of hollow supports 54 are fitted to the arm body 30 to guide the vertical movement of the central scraper 40. A vertically extending rod 56 is slidably inserted into each hollow support 54. The hollow supports 54, piston-cylinder assembly 46 and idler pulley 52 are all mounted on the arm body 30. A wire 62 with a chain is connected at one end to a piston rod 60 of a piston cylinder assembly 58 and at the other end to the end scraper 42 through an idler pulley 64 for vertical movement of the end scraper 42. A flexible scraping member 44 made of, for example, hard rubber, is also bolted to the lower end of the end scraper 42. Two end scrapers 42 are disposed touchably on the wall of the central pillar 24 and the side wall 28. Each of two end scrapers 42 is fitted to one end of two-arm levers 66 pivoted to the arm body 30. A weight 68 is secured to the other end of the arm lever 66. Where, therefore, the piston-cylinder assemblies 46, 58 are jointly actuated to pull or push the wires 50, 62, then the central scraper 40 and end scrapers 42 are moved upward or downward. The central scraper 40 is tightly attached by its own weight to the bottom board 26 of the chlorella-culturing tank 22, while the end scraper 42 is tightly pressed against the inclined peripheral wall of the frusto-conical central pillar 24 not only by its own weight but also by the rotating moment of the arm lever 66 resulting from the weight 68.

Figure 2:
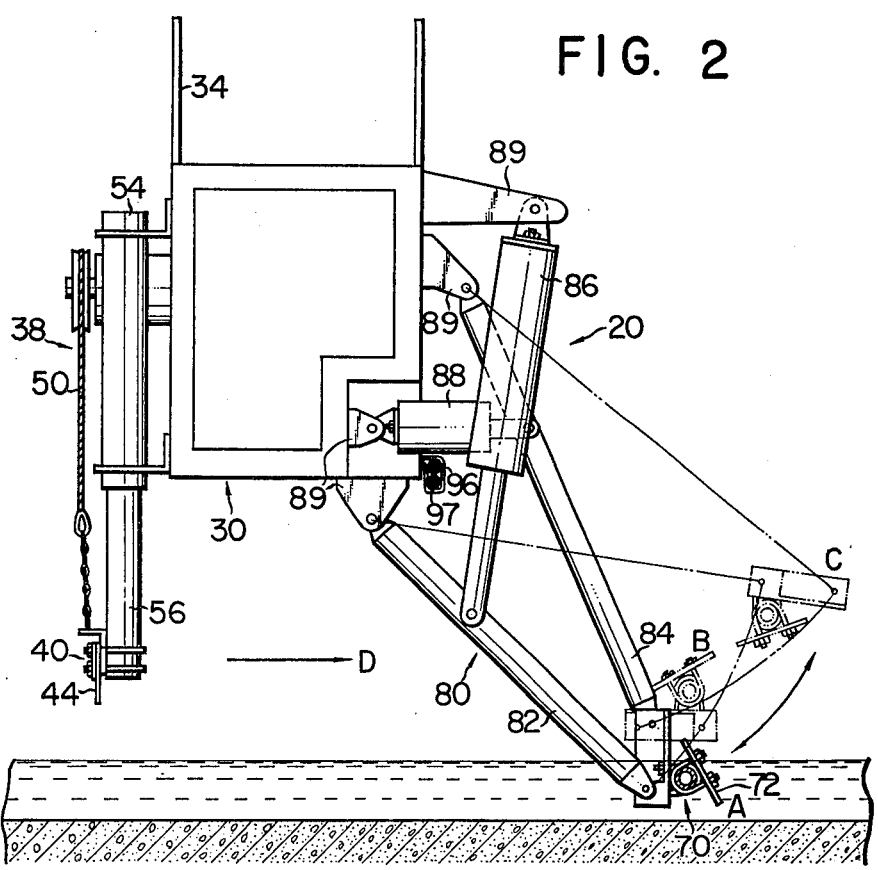
FIG. 2 is a side elevation of a rotatable arm body included in the chlorella-culturing apparatus of FIG. 1.
Figure 3:
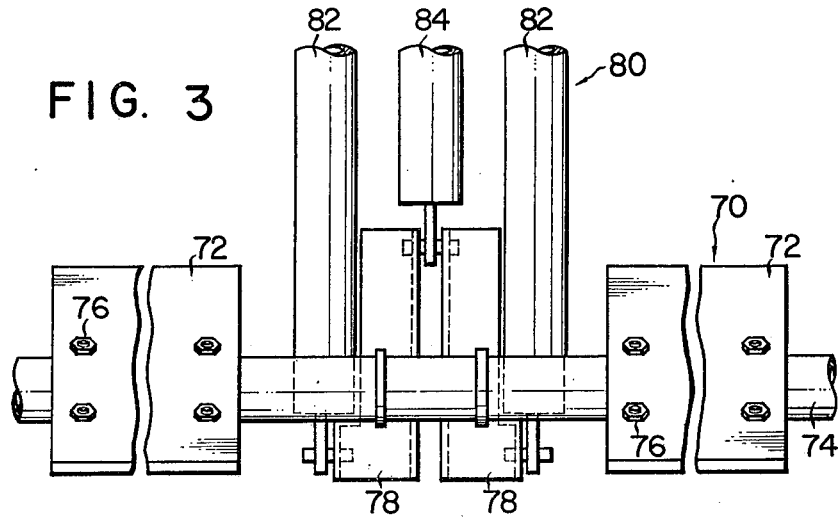
FIG. 3 is a front view of coupling means coupled to the stirring means.

As seen from FIG. 2, a stirring mechanism 70 is fitted to the forward corner side of the rotatable arm body 30 so as to swing independently of the rotation of said arm 30. A plurality of stirring blades 72 of the stirring mechanism are securely mounted on a support rod 74 (FIG. 3) by means of U-shaped bolts 76. The support rod 74 is fixed to two linearly arranged coupling or connecting boards 78 by U-shaped bolts 76. The connecting board 78 is made of channel steel as shown in FIG. 3. A notch is formed in the opposite or remotely separated edges of said linearly arranged two connecting boards 78.

A coupling mechanism 80 designed to mount the stirring mechanism 70 on the rotatable arm body 30 so as to allow the stirring mechanism 70 to swing independently of the rotation of the arm body 30 is of the link type interlockingly acting with the piston-cylinder assembly 46. The coupling mechanism 80 comprises two lower connecting rods 82 pinned to the outer or remotely separately edges of the two linearly arranged connecting boards 78, and a single upper rod 84 pinned to the mutually facing inner edges of said two connecting boards 78. Piston-cylinder assemblies 86, 88 are pivotted to the central part of the connecting rods 82, 84 respectively for their movement. Referential numeral 89 (FIG. 2) denotes fitting metal parts for pivotally supporting the connecting rods 82, 84 and piston cylinders 86, 88 respectively. Referring to FIG. 2, the piston-cylinder assemblies 86, 88 are pinned to the connecting rods 82, 84 respectively. However, connection between the piston-cylinder assemblies 86, 88 and connecting rods 82, 84 may be effected by other means. FIGS. 4 and 5 jointly illustrate a subject chlorella culturing apparatus, showing the different process of connecting the piston-cylinder assembly to the connecting rod from that which was applied in the preceding case. According to this modification, the piston-cylinder assembly 86 is pinned, as shown in FIG. 4, to a fitting board 92 fixed to an intermediate connecting rod 90 by the U-shaped bolt 76. A separate fitting board 94 is provided between the connecting rod 90 and lower connecting rod 82. The lower connecting rod 82 is fixed to the intermediate connecting rod 90 by means of the U-shaped bolt 76 from both sides of the fitting board 92.

The above-mentioned arrangement enables the lower connecting rod 82 to swing about the fitting metal part 89 in response to the reciprocation of the rod of the piston cylinder assembly 86. Obviously, connection between the piston-cylinder assembly 88 and upper connecting rod 84 may be effected by the aforesaid connecting process.

Under normal stirring condition, the stirring mechanism 70 constructed as described above carries out stirring at a position A indicated in FIG. 2. Where, however, the stirring blades have to be washed, the piston of the piston-cylinder assembly 88 is retracted to cause the upper connecting rod 84 to swing clockwise, and under this condition the piston of the piston cylinder assembly 86 is retracted to cause the lower connecting rod 82 to swing counterclockwise. Then the stirring mechanism 70 swings counterclockwise to occupy a position B. At the position B, the front side of the stirring blade 72 almost fully faces the arm body 30 for the object of washing, and can be thoroughly washed, for example, by an operator's spray of water from the arm body 30. Where, after the thorough washing of the front side of the stirring blade 72, the piston-cylinder assemblies 86, 88 are further operated to cause the stirring blade 72 to swing counterclockwise to a position C, then the backside of the stirring blade 72 almost fully faces the arm body 30 for the object of washing and can be thoroughly washed similarly by an operator's spray of water. The above-mentioned arrangement eliminates the necessity of emptying the chlorella-culturing tank 22 and causing an operator to enter said tank 22 for the washing of the stirring blades 72, and also efficiently carries out said washing easily from the arm body 30 for example, by an operator's spray of water when cultured chlorella is discharged together with the culturing liquid. Two ducts 97, 97a (FIG. 2) may be formed in the arm body 30 to wash the stirring blade 72. The duct 97 has a plurality of injection holes through which to eject water to the stirring blade 72 when it is brought to the position B. The duct 97a similarly has a plurality of injection holes through which to spray water to the stirring blade 72 when it is set at the position C. The same effect of washing can be attained by a single rotatable duct instead of the above-mentioned two ducts.

A support (not shown) is fitted to the arm body 30 for engagement with the backside of the lower connecting rod 82.

As previously described, the stirring mechanism 70 is mounted on the rotatable arm body 30 so as to swing independently of the rotation of said arm body 30. If, therefore, fixed to the rear side of the arm body 30, then the stirring mechanism 30 will be unable to overcome water resistance and buoyancy at the starting time or in case the liquid level of the chlorella-culturing tank 22 rises, and in consequence the stirring blades will float up, possibly decreasing the stirring efficiency. It is therefore advised, as in the foregoing embodiment, to dispose the stirring mechanism 70 on the forward corner side of the arm body 30.

As previously mentioned, the bottom board 26 of the circular chlorella-culturing tank 22 is radially inclined downward toward the peripheral edge of the tank 22. The bottom board 26 is formed with, as shown in FIGS. 6 and 7, a pair of discharging grooves 96 linearly extending in a radial direction and arranged symmetrical with respect to the central pillar 24. The discharging groove 96 has a rectangular cross section and may take an elongate tapered form progressively broadening toward the peripheral edge of the circular tank 22. When, therefore, brought down during the discharging step, the scraping mechanism 38 enables cultured chlorella to be quickly and easily drawn out through the discharging grooves 96. If a duct 98 is provided, as shown in FIG. 8, so as to vertically penetrate the frusto-conical central pillar 24 to force high pressure water streams into the discharging grooves 96 when the tank charge is removed, then the tank charge can be drawn out desirably at a high speed and with great ease.

Referring to FIG. 9, the lower end of the arm body 30 is fitted with water-spraying means 100 to eject water to the surface of the inclined wall of the frusto-conical central pillar 24 as well as of the inclined inner side wall 24 of the chlorella-culturing tank 22. This water-spraying means 100 consists of a duct 102, which comprises one T-shaped central portion for spraying water to the surface of the inclined wall of the frusto-conical central pillar 24 and two T-shaped end portions for ejecting water to the surface of the inclined inner side wall 28 of the chlorella-culturing tank 22. The duct 102 rotates with the arm body 30, carrying out full water spray on the surface of the inclined wall of the central pillar 24 as well as of the inclined inner side wall 28 of the tank 22 and in consequence effectively preventing cultured chlorella and any other material from being settled and gathered on said surface.

With the illustrated embodiment, the stirring mechanism 70 was made to swing by means of the piston-cylinder assemblies 86, 88. However, it is possible to effect the swing of the stirring mechanism 70 by fixing a sprocket wheel to the stirring blade-supporting rod 74 and properly operating a link chain engageable with the sprocket wheel. Further, the water-spraying means 100 may be disposed adjacent to the stirring blades 72 instead of being fixed to the arm body 30. With the illustrated embodiment, the scraping mechanism and stirring mechanism were separately provided. However, the stirring mechanism may be so arranged as to abut against the upper surface of the bottom board when the tank charge is removed. This arrangement makes it unnecessary to provide an independent scraping mechanism.

What we claim is:

1. A chlorella-culturing apparatus comprising a circular chlorella-culturing tank defined by an outer inclined side wall and a bottom board, a pillar positioned at the center of said tank, at least one rotatable arm body supported upon said pillar and extending from the pillar to said tank side wall, a stirring mechanism fitted to the lower part of said arm body forcefully to produce stirring streams by stirring blades, and a scraping mechanism mounted on said arm body so as to slide up and down and, when the tank charge is drawn out, the scraping mechanism may be brought down to abut against the upper surface of said bottom board and the surface of said inclined side wall of said tank, thereby scraping off deposits collected on said surface.

2. A chlorella-culturing apparatus according to claim 1 wherein said pillar has a frusto-conical form and the apparatus comprises means for spraying water on the surface of the inclined peripheral wall of the pillar and the inclined side wall of said tank.

3. A chlorella-culturing apparatus according to claim 2, wherein the water-spraying means is fitted to the arm body so as to rotate together.

4. A chlorella-culturing apparatus according to claim 3, wherein the scraping mechanism is fitted to a pair of rotatable arm bodies arranged diametrically symmetrical with respect to the central pillar of the chlorella-culturing tank, and a pair of discharging grooves rectangular in cross section are formed in the bottom board of the chlorella-culturing tank in diametrically symmetrical relationship with respect to said central pillar.

5. A chlorella-culturing apparatus according to claim 1, which further comprises means for coupling the stirring mechanism on the rotatable arm body to allow said stirring mechanism to swing independently of the rotation of the arm body.

6. A chlorella-culturing apparatus according to claim 5, wherein said coupling means includes at least two connecting rods, one side ends of which are pivotally supported at different points on the stirring mechanism, and two piston-cylinder assemblies whose piston rods are pivotally supported at the intermediate part of each connecting rod.

7. A chlorella-culturing apparatus according to claim 6, wherein the stirring mechanism includes a coupling element to which stirring blade-supporting rods are fixed and on which the connecting rods of the coupling means are pivotally supported.

8. A chlorella-culturing apparatus according to claim 7, wherein each piston-cylinder assembly is pivotally fitted to an intermediate connecting rod extending parallel with the stirring blade-supporting rod of the stirring mechanism, and said intermediate connecting rod is fixed to the connecting rods.

9. A chlorella-culturing apparatus according to claim 5, wherein the scraping mechanism is fitted to the rear side of the rotatable arm body, while the stirring mechanism is fitted to the front side thereof.

* * * * *